US008486067B2

(12) United States Patent
Anthony et al.

(10) Patent No.: US 8,486,067 B2
(45) Date of Patent: Jul. 16, 2013

(54) BONE GRAFT APPLICATOR

(75) Inventors: Sarah M. Anthony, Leesburg, IN (US);
Michael J. Brow, Parma, OH (US)

(73) Assignee: DePuy Synthes Products LLC, Warsaw, IN (US)

( * ) Notice: Subject to any disclaimer, the term of this patent is extended or adjusted under 35 U.S.C. 154(b) by 316 days.

(21) Appl. No.: 12/860,487

(22) Filed: Aug. 20, 2010

(65) Prior Publication Data

US 2011/0282403 A1    Nov. 17, 2011

Related U.S. Application Data

(60) Provisional application No. 61/345,324, filed on May 17, 2010.

(51) Int. Cl.
*A61B 17/56*     (2006.01)
(52) U.S. Cl.
USPC ................ 606/53; 623/16.11; 623/19.11
(58) Field of Classification Search
CPC .................................... A61B 17/1671
USPC ............. 606/53–58; 623/19.11–19.14, 16.11
See application file for complete search history.

(56) References Cited

U.S. PATENT DOCUMENTS

| 5,032,132 | A | 7/1991 | Matsen et al. |
| 5,195,856 | A * | 3/1993 | McSherry et al. ............... 411/55 |
| 6,458,136 | B1 | 10/2002 | Allard et al. |
| 6,911,047 | B2 | 6/2005 | Rockwood et al. |
| 2003/0125811 | A1 | 7/2003 | Bonutti |
| 2004/0034362 | A1 | 2/2004 | Abdelgany |
| 2004/0167617 | A1 | 8/2004 | Voellmicke |
| 2008/0183297 | A1 | 7/2008 | Boileau |

OTHER PUBLICATIONS

Rongeurs art labeled D1-D2 and accompanying statement, 3 pages, exact date unknown, prior to Aug. 2008.
European Search Report From Corresponding EPO App. No. 11164645.1-2 310, Dated Jul. 12, 2011, 7 Pages.

* cited by examiner

*Primary Examiner* — Thomas Sweet
*Assistant Examiner* — Jason-Dennis Stewart

(57) ABSTRACT

A bone graft applicator for applying bone graft to an orthopaedic implant. The bone graft applicator includes a pair of arms and a bone graft receptacle sized and shaped to be able to receive a portion of the orthopaedic implant within the receptacle. The bone graft receptacle is coupled to each of the pair of arms. The bone graft applicator also includes a linking mechanism. The linking mechanism includes a recess sized and shaped to extend at least partially around the portion of the orthopaedic implant and is coupled to the bone graft receptacle.

13 Claims, 9 Drawing Sheets

1

BONE GRAFT APPLICATOR

CROSS-REFERENCE TO RELATED APPLICATIONS

This application claims the benefit of U.S. Provisional Patent Application Ser. No. 61/345,324 entitled, "BONE GRAFT APPLICATOR", filed on May 17, 2010, which is hereby incorporated by reference in its entirety.

TECHNICAL FIELD

The present invention relates generally to an instrument for use in orthopaedic surgery, and more particularly to an instrument for grafting bone onto an orthopaedic implant.

BACKGROUND

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem that is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

In response to shortcomings associated with two-piece glenoid component designs, a number of one-piece glenoid components have heretofore been designed. In regard to such one-piece designs, a body portion, having a bearing surface defined therein for receiving the head of the humeral component, has a number of attachment pegs integrally formed therewith. The attachment pegs are advanced and thereafter secured into a corresponding number of holes that are drilled in the glenoid surface of the scapula by use of bone cement. An example of such a one-piece glenoid component that is designed to be secured to the scapula by use of bone cement is disclosed in U.S. Pat. No. 5,032,132 issued to Matsen, III et al.

Certain one-piece glenoid components have been designed to include finned-pegs, such as described in U.S. Pat. No. 6,911,047, which is herein incorporated by reference in its entirety. The fins act as barbs when the pegs are inserted into holes drilled in the scapula, securing the glenoid component to the scapula.

In some methods of inserting the finned-peg glenoid implant to the scapula, bone graft is inserted between the fins. Adding bone graft aids in the osseointegration of the implant into the scapula. However, there is currently not an instrument offered that places the bone graft onto the implant. Oftentimes, a member of the surgical team will use their gloved hands to apply the bone graft onto the pegs. However, the bone graft will often stick to the user's gloves, making this method of applying bone graft messy and imprecise.

Therefore, there is a need for an instrument to efficiently and adequately apply bone graft to a glenoid component.

Also, there is a need for an instrument that can efficiently and adequately apply bone graft to other orthopaedic implants.

SUMMARY OF THE INVENTION

According to one embodiment of the present application, a bone graft applicator for applying bone graft to an orthopaedic implant is provided. The bone graft applicator includes a pair of arms and a bone graft receptacle sized and shaped to be able to receive a portion of the orthopaedic implant within the receptacle. The bone graft receptacle is coupled to each of the pair of arms. The bone graft applicator further includes a linking mechanism, the linking mechanism including a recess sized and shaped to extend at least partially around the portion of the orthopaedic implant, the linking mechanism coupled to the bone graft receptacle.

According to another embodiment of the present invention, a method for applying bone graft to an orthopaedic implant is provided. The method includes using a bone graft applicator including a pair of arms, a bone graft receptacle coupled to the arms, and a linking mechanism coupled to the bone graft receptacle. The linking mechanism is slid over a portion of the orthopaedic implant and bone graft is scraped into the bone graft receptacle. The bone graft receptacle is closed over the portion of the orthopaedic implant. The bone graft applicator is removed from the orthopaedic implant.

According to yet another embodiment of the present invention, a kit for applying bone graft is provided and includes a glenoid component having a peg and a bone graft applicator. The bone graft applicator is sized and shaped to apply bone graft to the peg of the glenoid component. The bone graft applicator includes a pair of arms, a pair of cavities coupled to the pair of arms, and a linking mechanism coupled to the pair of cavities. The pair of cavities can be in an opened position such that one of the pair of cavities is located at an angle from the other of the pair of cavities and the angle is in the range of about 100 degrees to about 180 degrees.

BRIEF DESCRIPTION OF THE DRAWINGS

For a more complete understanding of the present invention and the advantages thereof, reference is now made to the following description taken in connection with the accompanying drawings.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
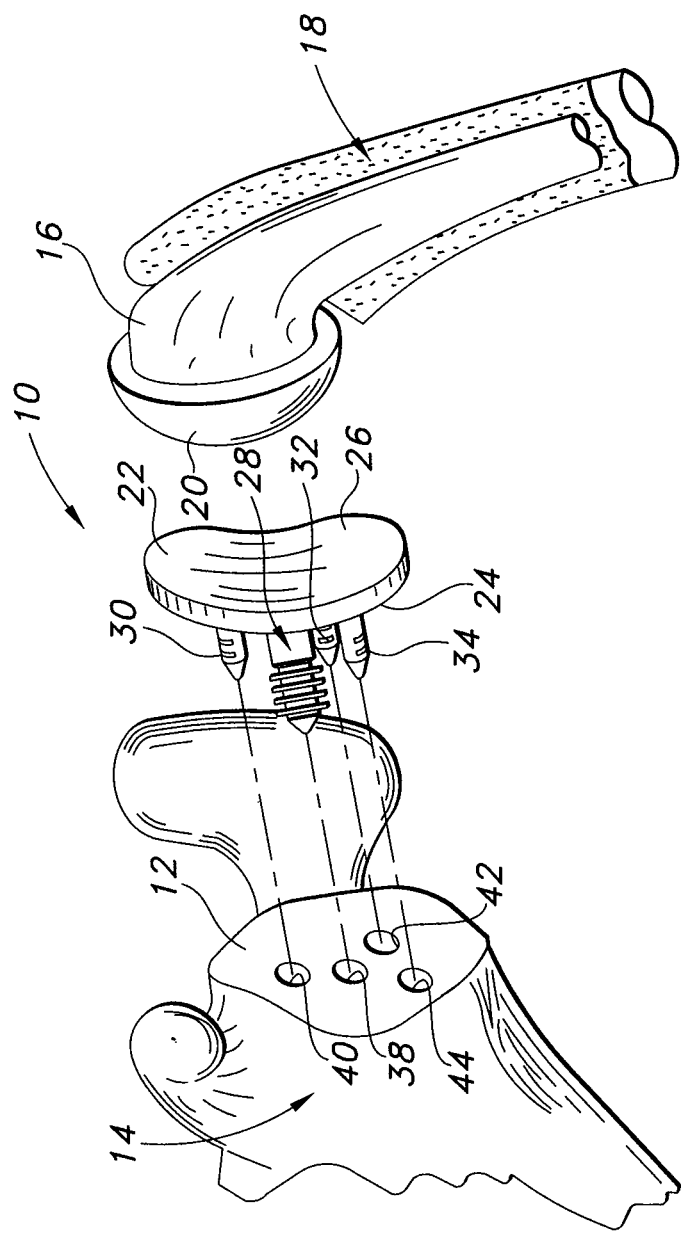
FIG. 1 is an exploded perspective view that shows a glenoid component positioned between a glenoid surface of a scapula and a humeral component.

Referring now to FIG. 1, there is shown a glenoid component 10 located between a glenoid surface 12 of a scapula 14 and a humeral component 16. The humeral component 16 has been implanted or otherwise secured to a humerus 18. As shall be discussed below in greater detail, the glenoid component 10 is configured to be secured to the glenoid surface 12 of the scapula 14 without the use of bone cement on an anchor peg 28 (discussed below) in order to replace the natural glenoid surface 12 during a total shoulder replacement procedure. In such a manner, the glenoid component 10 functions as a bearing surface for receiving a head portion of the humerus 18 (i.e. a head portion 20 of the humeral component 16 implanted in the humerus 18).

Figure 2:
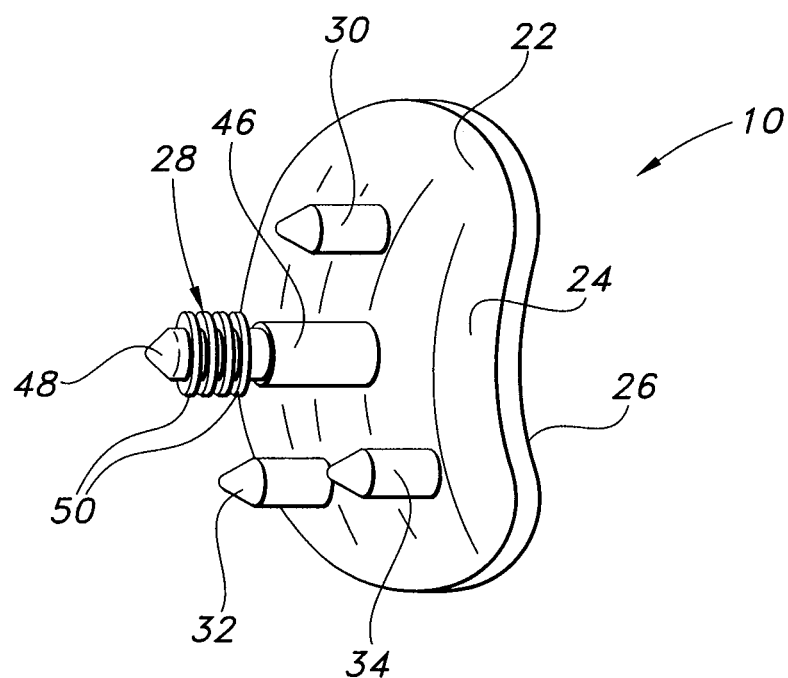
FIG. 2 is a perspective view of the glenoid component of FIG. 1.

As shown in FIGS. 1 and 2, the glenoid component 10 includes a body portion 22 having a first generally convex surface 24 and a second generally concave surface 26. The convex surface 24 is configured to abut or otherwise contact the glenoid surface 12 of the scapula 14 when the glenoid component 10 is secured thereto. The concave surface 26 of the body portion 22 provides a bearing surface for the head portion 20 of the humeral component 16 implanted into the humerus 18.

The glenoid component also includes the anchor peg (or central peg) 28 and a number of stabilizing pegs 30, 32, 34. The anchor peg 28 and the stabilizing pegs 30, 32, 34 are secured to the convex surface 24 of the body portion 22 and extend outwardly therefrom. As shown in FIG. 1, the anchor peg 28 is received into an anchor hole 38 which is drilled or otherwise formed in the glenoid surface 12 of the scapula 14, whereas the stabilizing pegs 30, 32, 34 are received into a number of respective stabilizing holes 40, 42, 44 which are also drilled or otherwise formed in the glenoid surface 12 of the scapula 14.

The anchor peg 28 includes a beveled shaft portion 46 that is secured at its proximal end to the convex surface 24. The distal end portion of the shaft portion 46 has a conical tip 48 defined therein which is provided as a "lead in" to facilitate insertion of the anchor peg 28 into the anchor hole 38 drilled in the glenoid surface 12 of the scapula 14.

In addition to the conical tip 48, the distal end portion of the shaft portion 46 also has a number of fins 50 (or flutes) secured thereto. The fins 50 extend radially outwardly from the shaft portion 46 of the anchor peg 28 in a substantially perpendicular direction relative to the shaft portion 46 such that the outer diameter of each of the fins 50 is greater than the outer diameter of the shaft portion 46. Each of the fins 50 preferably extends continuously around the entire outer periphery of the shaft portion 46, although the fins 50 may alternatively be embodied as a series of individual flange sections that line substantially all of the outer periphery of the shaft portion 46.

Figure 3:
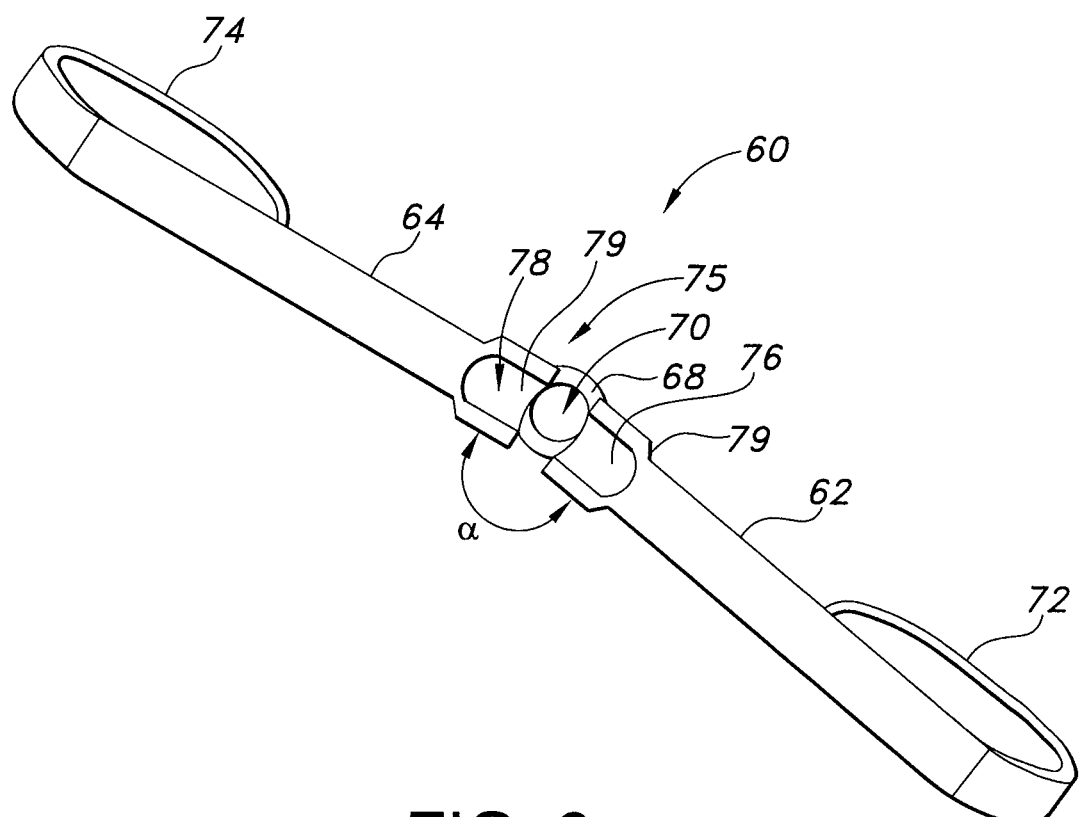
FIG. 3 is a perspective view of a bone graft applicator according to one embodiment of the present application in an open position.
Figure 4:
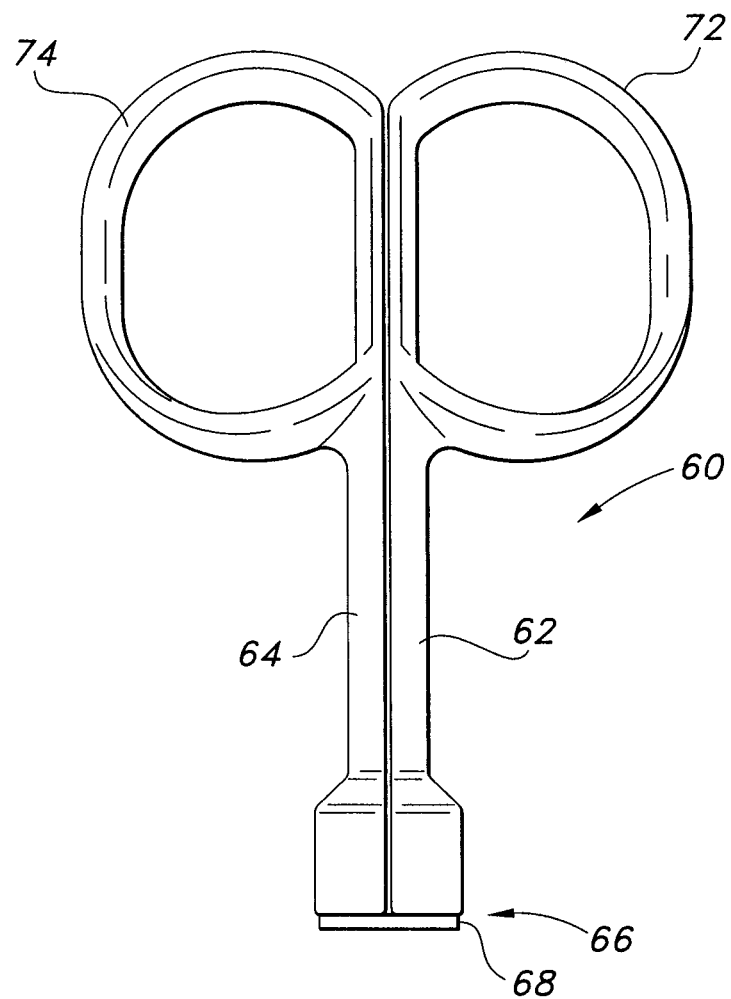
FIG. 4 is a perspective view of a bone graft applicator of FIG. 3 in a closed position.
Figure 5:
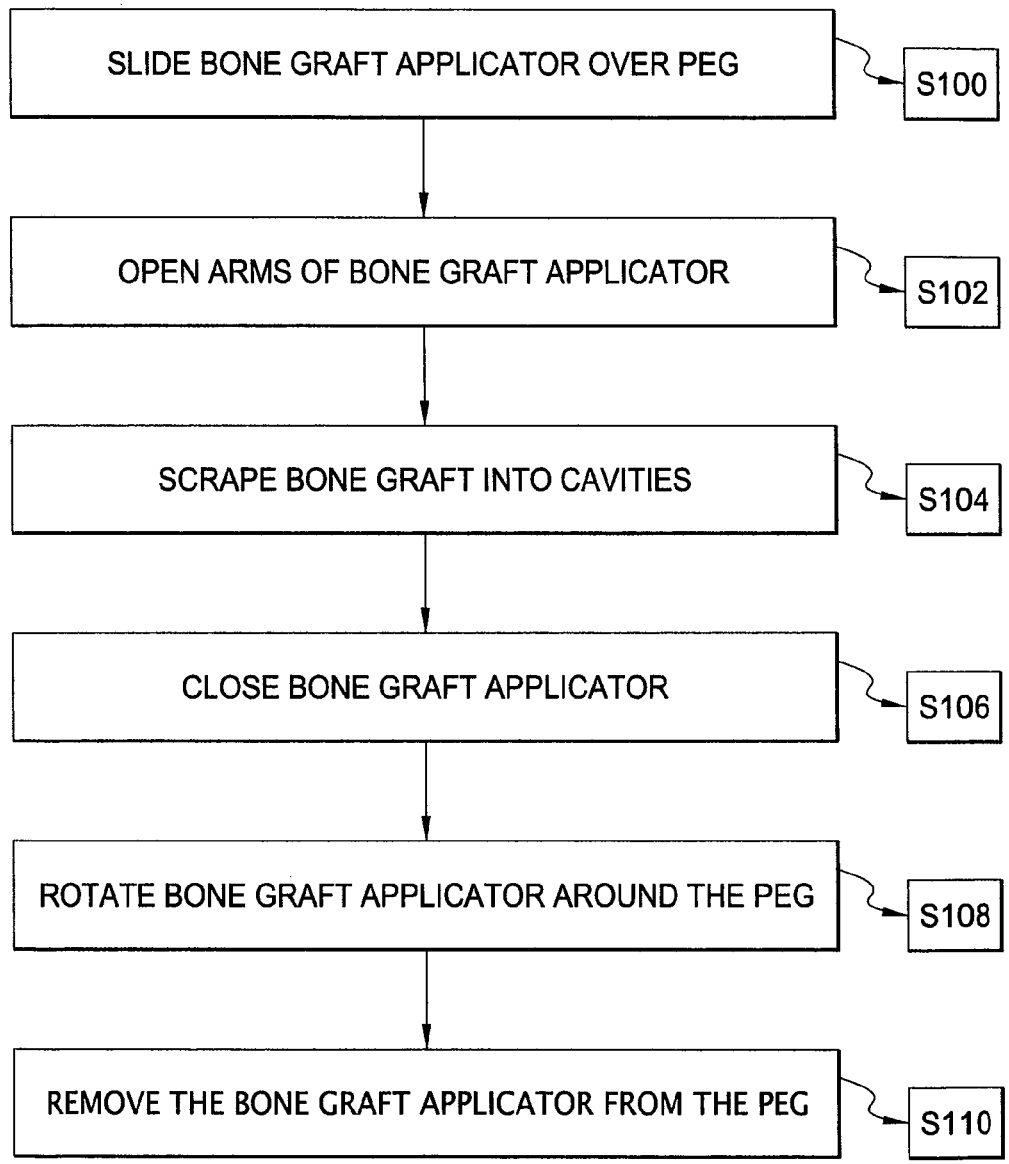
FIG. 5 is a flow chart illustrating the method of operating the bone graft applicator of FIG. 3.

As discussed above in the Background section, some surgeons desire to place bone graft onto the fins 50 and into the spaces between the fins 50 to aid in the bone integration of the implant. The bone graft may be taken from a number of places. In some embodiments, the bone graft is taken from drilling the anchor hole 38 of the glenoid. In other embodiments, it is taken from drilling the resected portion of the humeral head. To aid in this, according to one aspect of the invention, a bone graft applicator (or instrument) 60 is provided as shown in FIGS. 3 and 4. As shown, the bone graft applicator 60 includes a pair of arms 62, 64. The pair of arms 62, 64 are coupled via a linking mechanism 66. In this embodiment, the linking mechanism 66 is a ring 68. The ring 68 includes a recess 70 that is sized and shaped to receive the fins 50 of the glenoid component 10. In this embodiment, the linking mechanism 66 is sized and shaped to slide over and around the portion of the implant that is to receive the bone graft. In other embodiments, the linking mechanism 66 may extend only partially around the portion of the implant that is to receive the bone graft. In yet other embodiments, the linking mechanism 66 may not be able to slide over the portion of the implant, but may still extend partially around that portion. As shown in FIGS. 3 and 4, each of the arms 62, 64 includes a handle 72, 74. The handles 72, 74 allow the user to grasp the applicator 60. In some embodiments, the handles 72, 74 may not be included and the user may grasp the arms 62, 64.

As shown in FIG. 3, the arms 62, 64 are coupled to a bone graft receptacle 75. In the illustrated embodiment, the bone graft receptacle 75 includes a pair of cavities 76, 78. The cavities 76, 78 are coupled to and adjacent to the linking mechanism 66. The cavities 76, 78 are each linked to the linking mechanism 66 via a hinge 79. The hinge allows the cavities 76, 78 (and thus the arms 62, 64) to open and close as shown in FIGS. 3 and 4. Specifically, the hinge 79 allows the cavities 76, 78 (and thus arms 62, 64) to open to a large angle α (defined as the angle between the two arms 62, 64). In one embodiment, the angle α is between about 100 and about 180 degrees. Preferably, the angle α is between about 170 and about 180 degrees. By having the arms opened wide, the cavities 76, 78 are easier to fill with the bone graft. The cavities 76, 78 are sized and shaped to receive the bone graft. When the arms are in a closed position as shown in FIG. 4, the cavities 76, 78 create a single cavity that is sized and shaped to receive the anchor peg 28 (as will be shown in FIG. 7 below).

Figure 6:
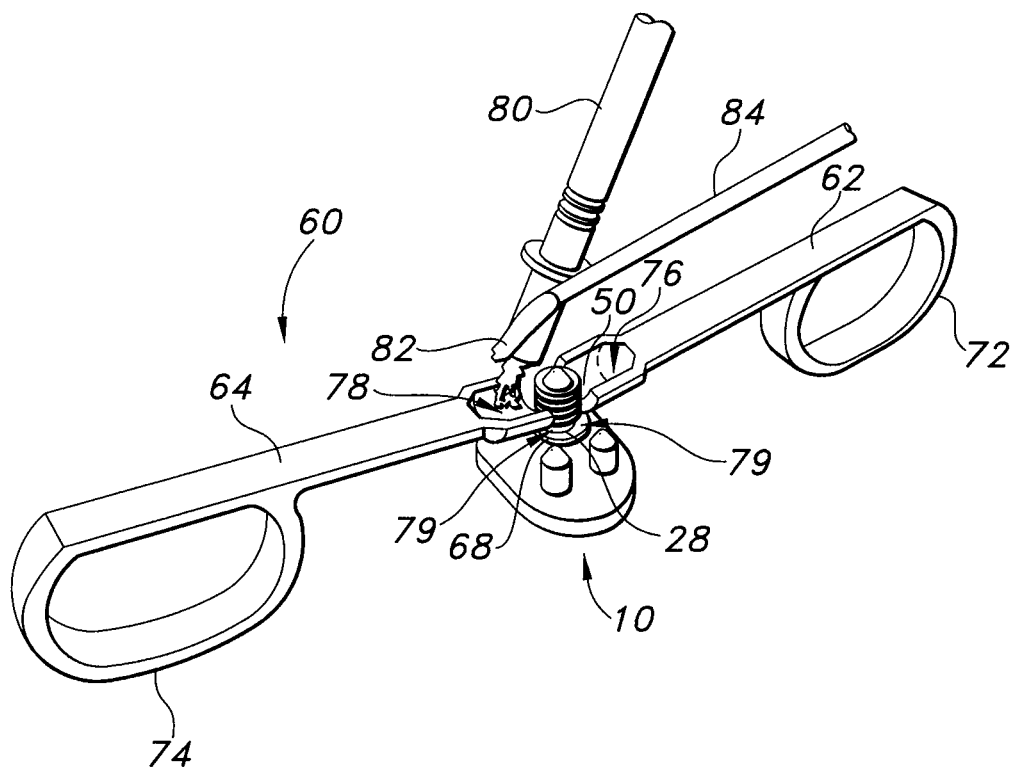
FIG. 6 is a perspective view of the bone graft applicator of FIG. 3 and a glenoid component of FIG. 1 in use.

Turning now to FIGS. 5-8, a flow chart illustrating the method of using the bone graft applicator 60 is shown. First, at step s100, the bone graft applicator 60 is slid over the anchor peg 28, which may be sitting on a table with the articular surface down and anchor peg 28 up. The arms 62, 64 of the applicator 60 are then opened as shown in FIG. 6 at step s102, exposing the fins 50. In some embodiments, the applicator may be in an open position prior to being slid over the anchor peg. As shown in FIG. 6, the ring 68 slides over (and thus extends around) the anchor peg 28 and fins 50. In other words, the recess 70 (which is in this embodiment, a circular opening) is slid over the anchor peg 28. Next, at step s104, the bone graft (also known as bone paste) is scraped into the cavities 76, 78. The bone graft should be placed into both cavities 76, 78. In the illustrated embodiment, as shown in FIG. 6, an instrument 80 holds bone graft 82. A scraper 84 is used to scrape the bone graft 82 out of the instrument 80 and into the cavities 76, 78 of the bone graft applicator 60. In other embodiments, other tools or methods for applying the bone graft to the cavities 76, 78 may be used.

Figure 7:
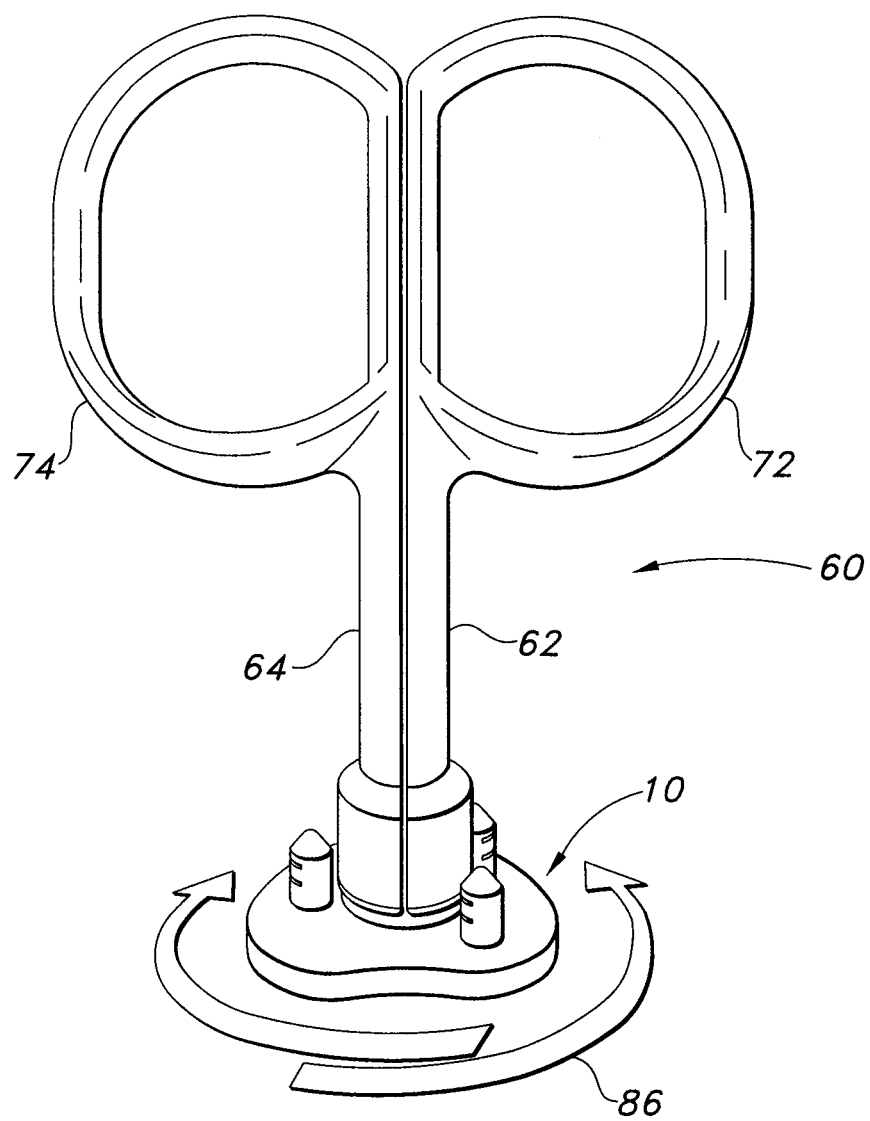
FIG. 7 is a perspective view of the bone graft applicator of FIG. 3 applying bone graft to the glenoid component of FIG. 1.
Figure 8:
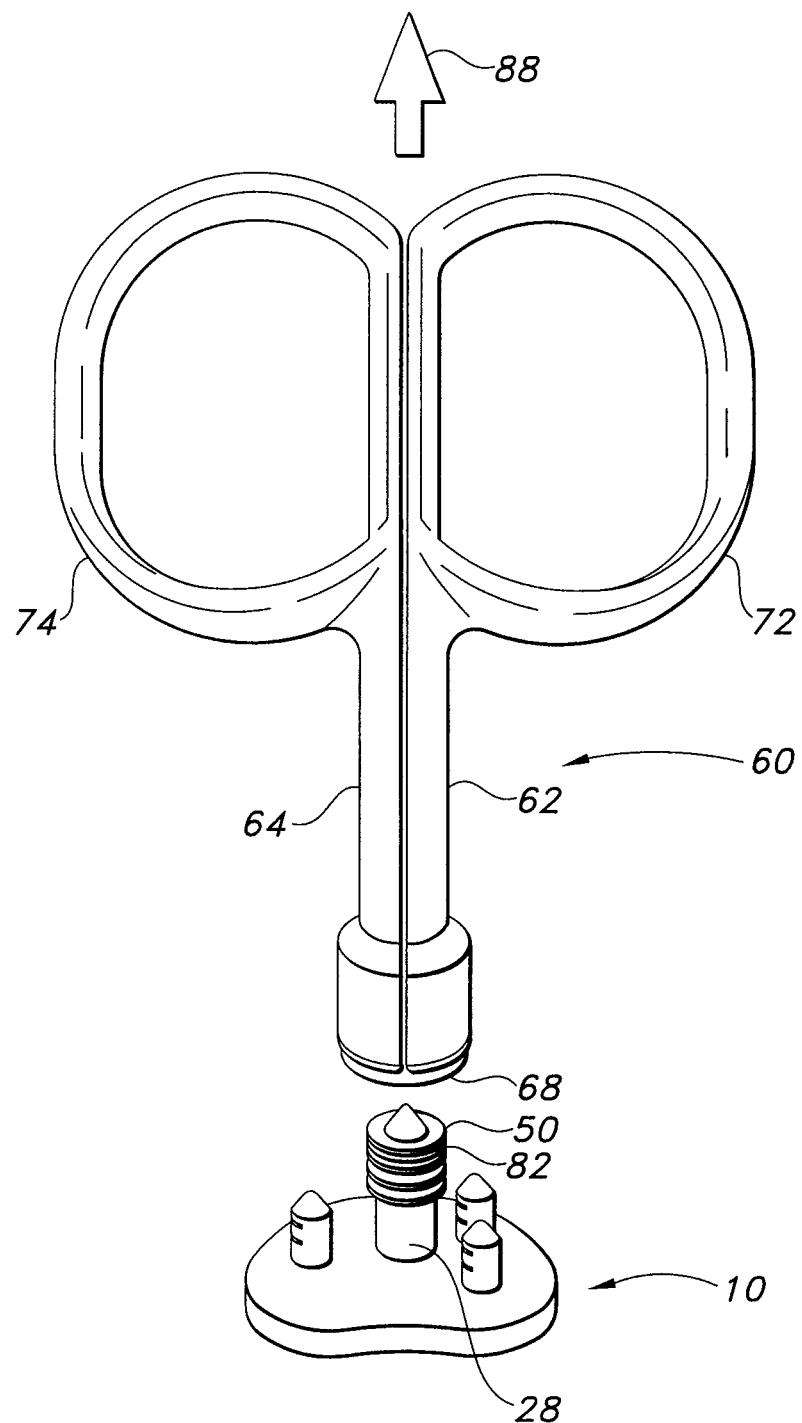
FIG. 8 is a perspective view of the bone graft applicator of FIG. 3 after it has been removed from the glenoid component of FIG. 1.

At step s106, the bone graft applicator 60 is closed over the anchor peg 28 and its fins 50 (shown in FIG. 7). The two cavities 76, 78 surround the anchor peg 28 and apply the bone graft 82 in between the fins 50. In the present embodiment, the bone graft applicator 60 applies the bone graft equally to both sides simultaneously. The two cavities 76, 78 surround the peg at the same time, are perpendicular to the ground, and are equally affected by the effects of gravity, thereby applying the bone graft equally (and simultaneously) around the peg 28. The bone graft applicator is then rotated about the anchor peg 28 in the direction shown by arrows 86 in FIG. 7 at step s108 while the anchor peg 28 is held in place (to keep from rotating). The rotation further embeds the bone graft 82 in between the fins 50. With the bone graft applicator 60 still in a closed position, the bone graft applicator is then removed from the anchor peg 28 (step s110). As shown in FIG. 8, bone graft 82 fills in the space between the fins 50. Removal of the bone graft applicator is easy since the bone graft applicator 60 is kept closed. Also, since the cavities 76, 78 are closed, any bone graft 82 that is not affixed to the fins 50 is less likely to spill out of the applicator 60. Furthermore, removal along the axis as indicated by the arrow 88 compresses the bone graft 82 into the fins 50 and prevents migration of the bone graft 82 out of the sides of the fins 50.

Figure 9:
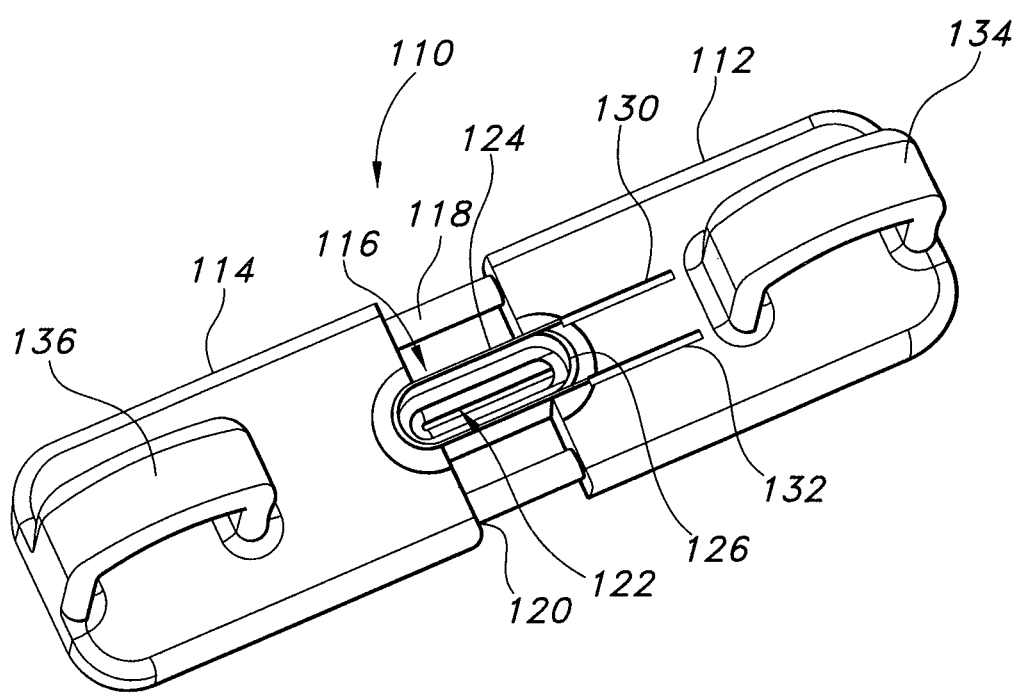
FIG. 9 is a perspective view of a bone graft applicator according to another embodiment of the present invention.

Turning now to FIG. 9, another embodiment of a bone graft applicator 110 will be described. In this embodiment, the bone graft applicator 110 includes a pair of arms 112, 114. The pair of arms 112, 114 are coupled via a linking mechanism 116. In this embodiment, the linking mechanism 116 is a pair of rods 118, 120 and a u-shaped wall 124 and an arcuate wall 126. The pair of rods 118, 120 extends from one arm 112, 114 into a recess on the other arm 112, 114 (not shown). The u-shaped wall 124 and arcuate wall 126 also define the bone graft receptacle 125. In this embodiment, the bone graft receptacle includes a shaped cavity 122. The arm 112 also includes two channels 130, 132 that receive the ends of the u-shaped wall 124. In use, the user will place the anchor peg 28 (FIGS. 1 and 2) into the applicator 110. After the bone graft is poured into the cavity 122, the two arms 112, 114 are slid together, causing the ends of the u-shaped wall 124 to slide into the channels 130, 132 and decrease the size of the shaped cavity 122. The bone graft is then forced into the fins 50 as the arcuate wall 126 comes closer to the end of the u-shaped wall 124. By moving the arms 112, 114, the bone-shaped cavity is then sized and shaped to abut the fins 50 on the anchor peg 28 and to apply the bone graft into the fins 50. In the illustrated embodiment, the arms 112, 114 of the applicator 110 include handles 134, 136. In some embodiments, there may not be handles, and the user may just grasp the arms.

In some embodiments, the applicators 60, 110 may be made of stainless steel. In other embodiments, the applicators 60, 110 may be made of plastic. Other materials may also be used. As shown in the embodiments of FIGS. 1-4 and 6-8, each of the cavities 76, 78 and each of the arms 62, 64, 112 and 114 are a single piece. However, in other embodiments, the cavity and the arms may be separate pieces and may be coupled using any known method.

The above embodiments both describe using the bone graft applicator to apply bone graft to a peg on a glenoid component. However, the bone graft applicator may also be used to apply bone graft to pegs located on knee implants, such as a patellar component, a femoral component, or a tibial component. In each of these cases, the linking mechanism of the bone graft applicator should include a recess large enough to be able to extend around the peg. Also, the cavities of such a bone graft applicator would be sized and shaped to accommodate peg of the implant. The applicator of the present invention may also be used on other orthopaedic components such as acetabular hip cups, cement plugs, or other pegged implants. In some embodiments, the pegs of the implants may not be finned (in other words, do not include fins). In these cases, if the peg includes a porous coating, the bone graft would be able to stick to the porous coating.

Although the present invention and its advantages have been described in detail, it should be understood that various changes, substitutions, and alterations could be made therein without departing from the spirit and scope of the present invention as defined by the appended claims.

We claim:

1. A bone graft applicator for applying bone graft to an orthopaedic implant, the bone graft applicator comprising:
   a pair of arms;
   a bone graft receptacle sized and shaped to be able to receive a portion of the orthopaedic implant within the receptacle, the bone graft receptacle coupled to each of the pair of arms; and
   a linking mechanism, the linking mechanism including a recess sized and shaped to extend at least partially around the portion of the orthopaedic implant, the linking mechanism coupled to the bone graft receptacle; wherein the bone graft receptacle includes a pair of cavities, one of the pair of cavities coupled to one of the pair of arms and the other of the pair of cavities coupled to the other of the pair of arms.

2. The bone graft applicator of claim 1, wherein each of the pair of cavities is linked to the linking mechanism via a hinge.

3. The bone graft applicator of claim 1, wherein the linking mechanism is a ring defining a recess.

4. The bone graft applicator of claim 1, wherein the recess is sized and shaped to fit over the portion of the orthopaedic implant.

5. The bone graft applicator of claim 1, wherein each of the pair of arms includes a handle.

6. The bone graft applicator of claim 1, wherein the linking mechanism includes a u-shaped wall and an arcuate wall.

7. A kit for applying bone graft, the kit comprising:
   a glenoid component having a peg; and
   a bone graft applicator sized and shaped to apply bone graft to the peg of the glenoid component, the bone graft applicator including a pair of arms, a pair of cavities coupled to the pair of arms, and a linking mechanism coupled to the pair of cavities, wherein the pair of cavities can be in an opened position such that one of the pair of cavities is located at an angle from the other of the pair of cavities and the angle is in the range of about 100 degrees to about 180 degrees.

8. The kit of claim 7, wherein the peg has a plurality of fins and the bone graft applicator is sized and shaped to apply bone graft between the plurality of fins.

9. The kit of claim 7, wherein the peg includes a porous coating and the bone graft applicator is sized and shaped to apply bone graft into pores of the porous coating.

10. The kit of claim 7, wherein the linking mechanism is sized and shaped to extend around the peg.

11. The kit of claim 10, wherein the linking mechanism is a ring defining a recess, the recess having a diameter larger than the peg.

12. The kit of claim 10, wherein the linking mechanism is a moveable u-shaped wall and an arcuate wall.

13. The kit of claim 10, wherein the linking mechanism is coupled to the pair of cavities via hinges.

* * * * *